United States Patent [19]

Namba

[11] Patent Number: 4,828,388
[45] Date of Patent: May 9, 1989

[54] METHOD OF MEASURING CONCENTRATION OF SUBSTANCES

[75] Inventor: Akihiro Namba, Tokyo, Japan
[73] Assignee: Olympus Optical Co., Ltd., Japan
[21] Appl. No.: 59,619
[22] Filed: Jun. 8, 1987

[30] Foreign Application Priority Data

Jun. 11, 1986 [JP] Japan .................. 61-135782

[51] Int. Cl.$^4$ .................. G01N 33/543; G01N 21/47
[52] U.S. Cl. .................. 356/336; 356/339
[58] Field of Search ............... 356/335, 336, 338, 339

[56] References Cited

U.S. PATENT DOCUMENTS 4,139,303  2/1979  Carlson et al. ............ 356/336
4,259,015  3/1981  Wada ....................... 356/336

FOREIGN PATENT DOCUMENTS 3117272  3/1982  Fed. Rep. of Germany.
3525719  1/1986  Fed. Rep. of Germany.
3531891  3/1986  Fed. Rep. of Germany.

OTHER PUBLICATIONS

Howard A. Strobel: Chemical Instrumentation, Second Edition, Addison-Wesley Publishing Company, Reading, Mass., 1973, pp. 581-591.

Primary Examiner—Richard A. Rosenberger
Attorney, Agent, or Firm—Arnold, White & Durkee

[57] ABSTRACT

A concentration of antigen substances contained in a sample is measured by detecting light scattered by latex particles coated with antibody substances which are specifically reactive with the antigen substances to be measured. The scattered light is received by a photodetector and an output signal of the photodetector is supplied to a fast Fourier transform unit to derive a power spectrum density of the scattered light. Then a white level of the power spectrum density is derived, and the concentration of the antigen substances in the sample is detected from the white level with the aid of a calibration curve representing a relationship between the concentration and the white level.

10 Claims, 8 Drawing Sheets

FIG_4

FIG_6A
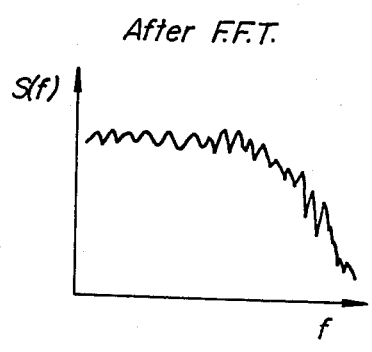
FIG_6B
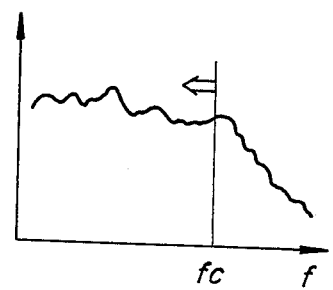
FIG_6C
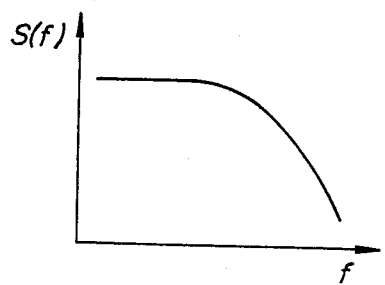

FIG_7
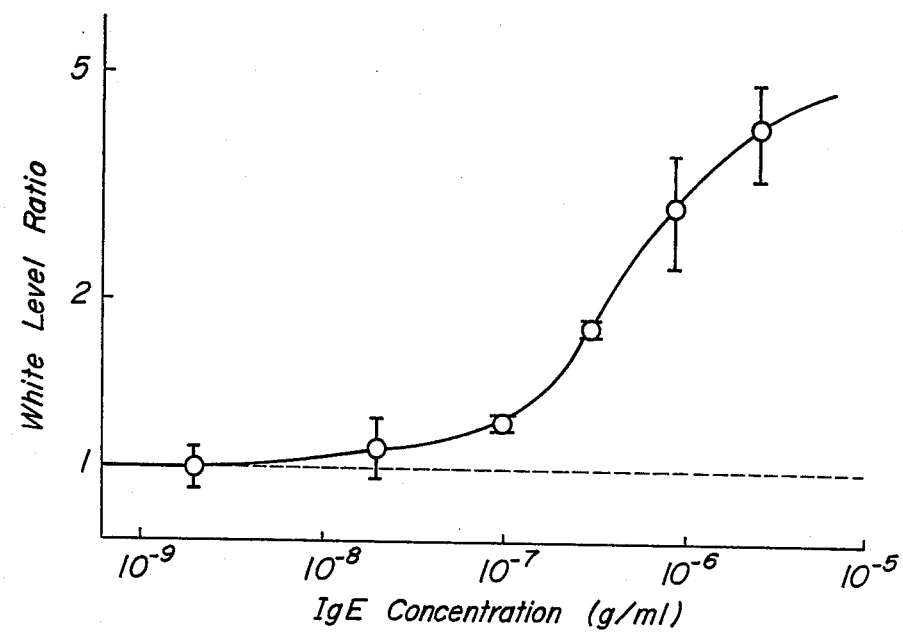
FIG_8
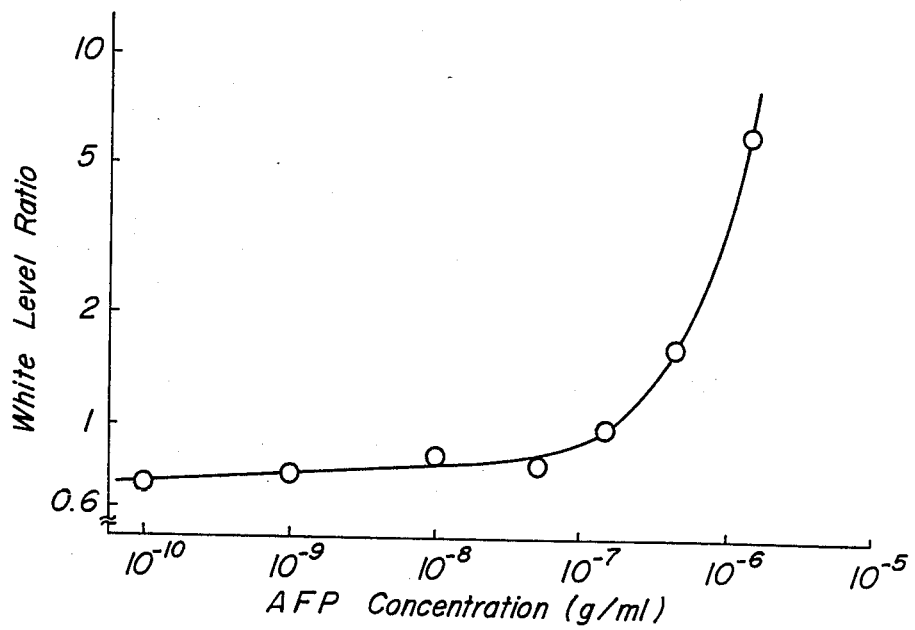

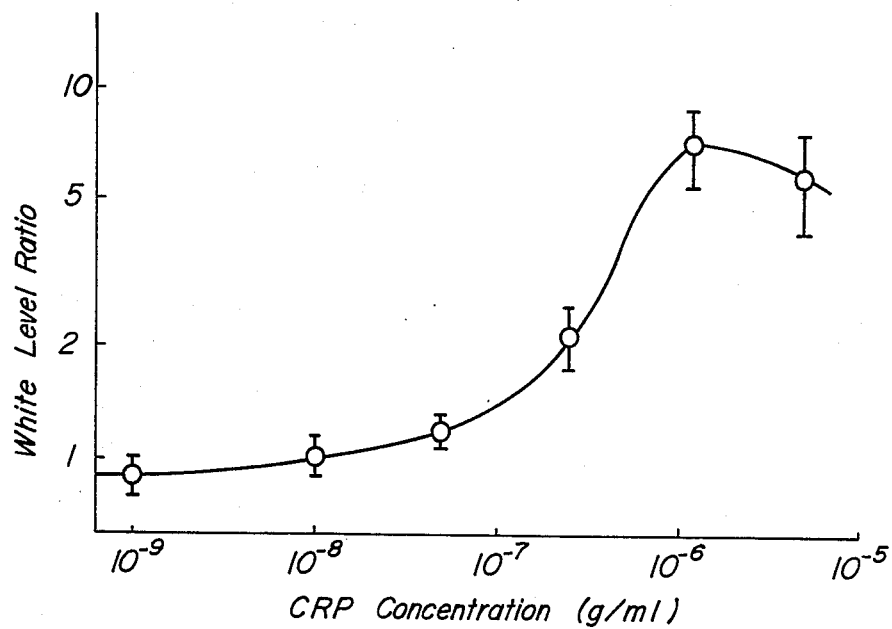
FIG_9

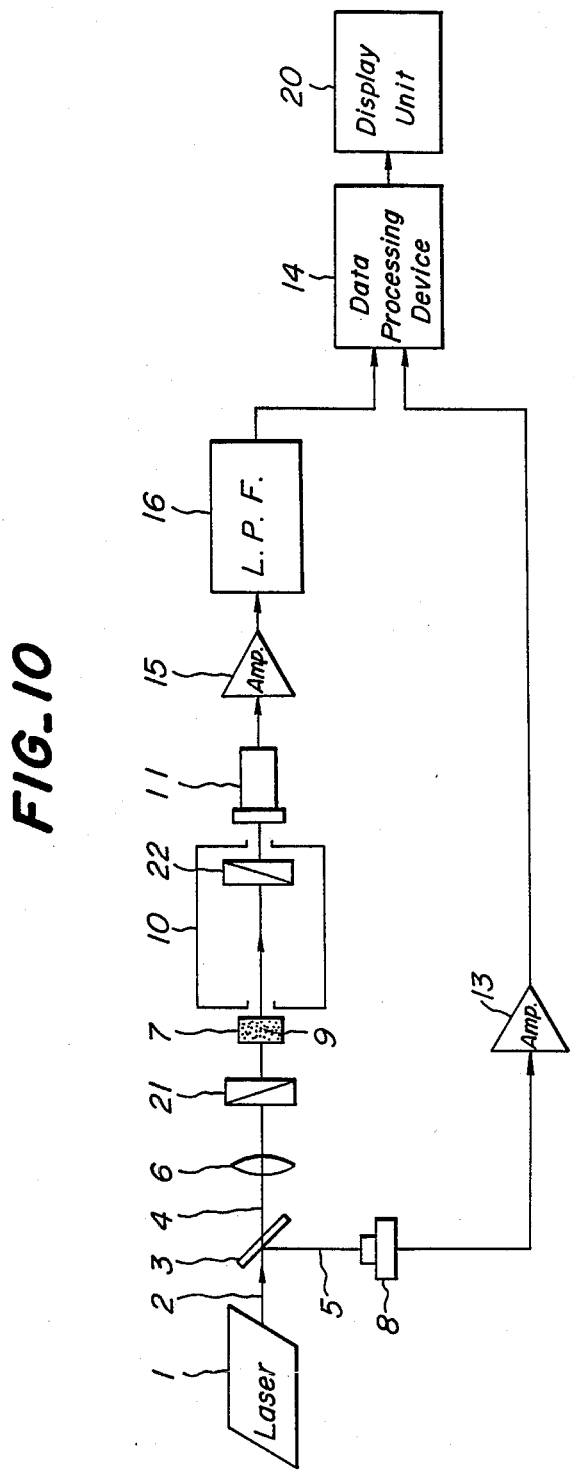

METHOD OF MEASURING CONCENTRATION OF SUBSTANCES

BACKGROUND OF THE INVENTION

1. Field of the Invention and Related Art Statement

This invention relates to a method of measuring a concentration of substances contained in a sample by using a specific reaction between the substances in the sample and substances which are specifically reactive with the substances in the sample.

Such a specific reaction may be an immunological reaction between antigens and antibodies and a specifically bounding reaction, e.g., between biotin and avidin.

There has been proposed a method of measuring a concentration of substances contained in a sample by utilizing a power spectrum density of a fluctuation in intensity of scattered light. Such a method has been disclosed in Japanese Patent Application Laid-open Publication No. 61-28,866, corresponding to U.S. Pat. application Ser. No. 754,272 filed on July 12, 1985. In this method, the concentration is measured by utilizing the fact that a concentration of antigen or antibody substances is intimately related to a relaxation frequency of the power spectrum density of the fluctuation in intensity of light scattered from an antigen-antibody reaction liquid. That is to say, in this method, after the power spectrum density is derived, its relaxation frequency is derived, and finally the concentration is derived from the relaxation frequency.

In the method mentioned above, in order to measure the concentration of substances in a precise manner, it is necessary to derive the relaxation frequency accurately. However, it is difficult in practice to determine the relaxation frequency from a very wide frequency range.

SUMMARY OF THE INVENTION

The object of the present invention is to provide a novel and useful method of measuring a concentration of substances contained in a sample in an accurate manner by utilizing the power spectrum density of the fluctuation in intensity of scattered light without deriving the relaxation frequency.

According to the invention, a method of measuring a concentration of substances contained in a sample comprises the steps of:

projecting a radiation beam onto complexes which are produced by a specific reaction between substances contained in a sample to be measured and substances which are specifically reactive with the substances in the sample;

detecting radiation scattered by the complexes to provide a photoelectrically converted output signal;

deriving a power spectrum density of scattered radiation from the output signal;

deriving a white level or white level ratio of the power spectrum density; and deriving a concentration of the substances contained in the sample on the basis of the derived white level or white level ratio.

The inventor has experimentally found that the white level or white level ratio of the power spectrum density of light scattered by the complexes is intimately correlated with the concentration of substances contained in a sample to be measured. Therefore, by detecting the white level or white level ratio of the power spectrum of the fluctuation in intensity of light scattered by the complexes it is possible to measure the concentration of the specific substances in sample without deriving the relaxation frequency.

In the present specification, the substances contained in the sample are sometimes called sample substances, and the substances which are specifically reactive with the sample substances are sometimes termed reagent substances. There are many combinations of the sample substnces and the reagent substances, i.e. antigen and antibody, biotin and avidin, IgG (immunoglobuline G) and protein A, and other protein substances which are specifically reactive with each other. Further, the reagent substances may be bound on insoluble carriers such as latex particles.

BRIEF DESCRIPTION OF THE DRAWINGS

FIGS. 6A, 6B and 6C are graphs illustrating the effect of a method of smoothing the power spectrum density curve;

FIG. 7 is a graph illustrating a relationship between IgE concentration and white level;

FIG. 8 is a graph illustrating a relationship between AFP concentration and white level;

FIG. 9 is graph illustrating a relationship between CRP concentration and white level; and FIG. 10 is a schematic block diagram of a further embodiment of the apparatus for carrying out method according to the invention.

DESCRIPTION OF THE PREFERRED EMBODIMENTS

Figure 1:
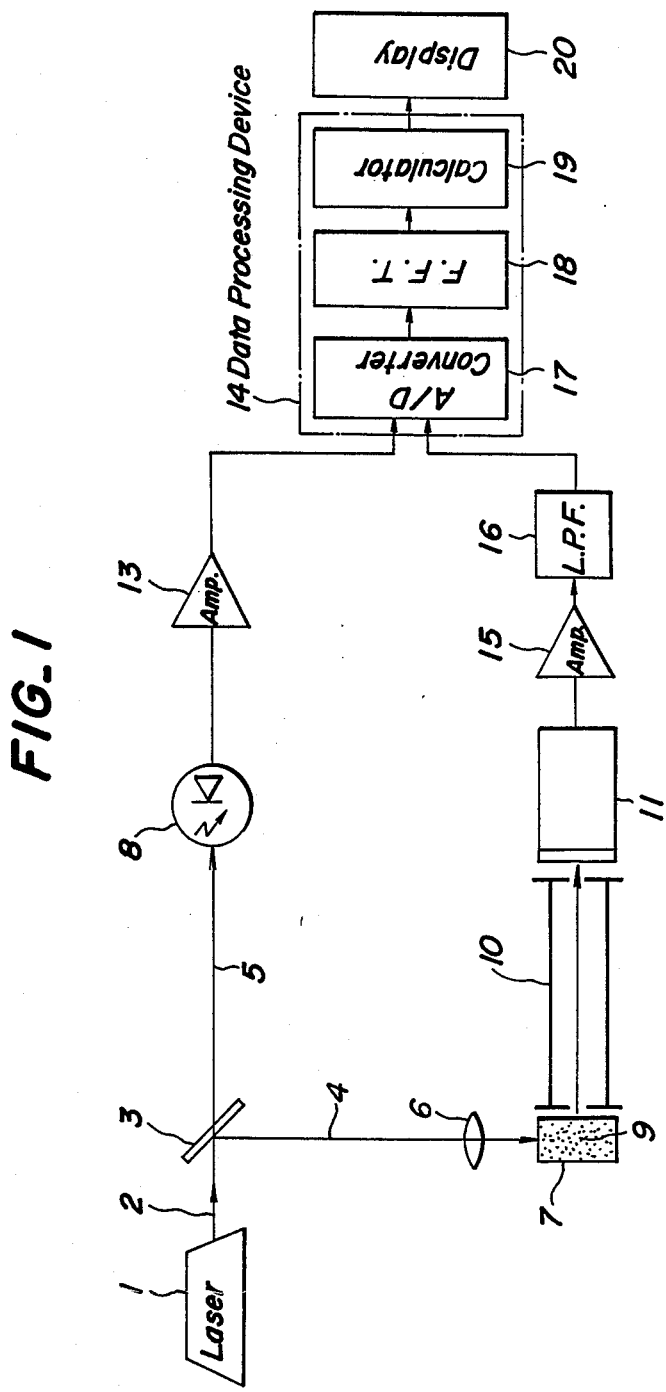
FIG. 1 is a schematic block diagram of an embodiment of apparatus for carrying out the method according to the invention.

FIG. 1 is a schematic block diagram of apparatus for carrying out an embodiment of the concentration measuring method according to the invention.

Although a coherent light source or an incoherent light source may be used in accordance with the present invention, present embodiment to employs a light source 1 for emitting coherent light which is constructed from a He-Ne gas laser emitting a laser beam (wavelength of 632.8 nm). The laser light flux or beam 2 emitted from the light source 1 is divided by a half mirror 3 into two light beam 4 and 5. Light beam 4 is collected by a condenser lens 6 and directed to impinge upon a cell 7 made of transparent material. Light beam 5 is directed to impinge upon a photodetector 8 such as a silicon photodiode which generates a monitor signal representing a variation of the intensity of the light beam 2 emitted from the light source 1.

Cell 7 contain a test liquid which is a mixture of a sample containing substances whose concentration is to be meaured and of reagent substances which are specifically reactive with the sample substances. In this embodiment the reagent substances are immobilized on outer surfaces of particles 9. Therefore, when the specific reaction occurs in the cell 7, attractive forces are generated between particles 9. Then the particles 9 are agglutinated with each other to form aggregates or complexes, and the Brownian motion of the complexes is changed in accordance with the size and shape of the complexes. Light rays scattered by the particles 9 and their aggregates in the cell 7 are directed to impinge upon a photodetector 11 via a collimator 10 having a pair of pin holes. The photodetector 11 is formed by a photomultiplier having a very high sensitivity.

The output monitor signal from the photodetector 8 is supplied via a low noise amplifer 13 to a data processing device, generally denoted 14, which is also supplied with an output signal from the photodetector 11 by means of low noise amplifier 15 and low pass filter 16. The data processing device 14 comprises an A/D converter unit 17a, fast Fourier transform (FFT) unit 18 and a calculation unit 19, and processes the signals as will be explained hereinafter to derive a concentration of the sample substances. The measured concentration is displayed by a display device 20.

The output signal from the photodetector 11, which represents an intensity of the scattered light emanating from the measuring cell 7, is normalized by the monitor signal supplied from the photodetector 8 and averaged for a short time period so that any fluctuation due to variation in the intensity of the laser light beam 2 emitted from the light source 1 is attenuated. Next, a power spectrum density of the fluctuation in intensity of the scattered light is detected, and the concentration of the sample substances is measured using the power spectrum density.

Figure 2:
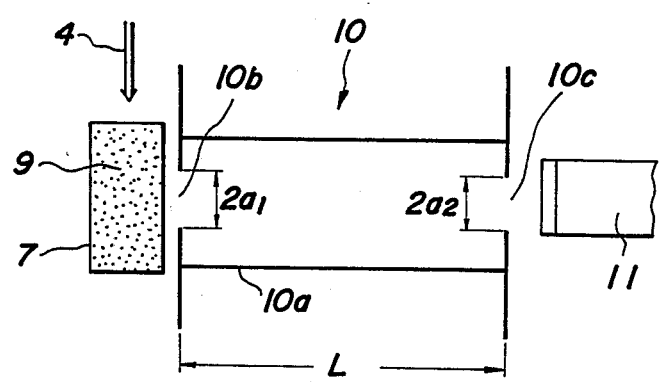
FIG. 2 is an enlarged schematic cross sectional view of a collimator illustrated in FIG. 1.

FIG. 2 is an enlarged schematic view showing in more detail the construction of the collimator 10 shown in FIG. 1. The collimator 10 comprises a tube 10a which is made of opaque material so as to remove the influence of external light. Further, an inner wall of the tube 10a is provided with an anti-reflecting coating. Pin holes 10b and 10c are provided in both ends of the tube 10a. Defining the radii of the pin holes 10b and 10c a $a_1$ and $a_2$, respectively, the distance between the pin hole as L, the refractive index of a medium inside the tube 10a as n, and the wavelength of the light as $\lambda$, the collimator 10 is constructed so as to satisfy the following equation (1).

$$L \geq \frac{4n \cdot a_1 \cdot a_2}{\lambda} \quad (1)$$

According to the invention, the power spectrum density of the fluctuation in intensity of scattered light is detected. The power spectrum density can be represented by a fluctuation term due to interference of light which is caused by randomly moving particles, and a fluctuation term due to a number of particles which enter into and go out of a scattering volume. The first fluctuation term due to the interference is observed as a spatial fluctuation of a speckle pattern. If this spatial fluctuation is detected by a photodetector having a wide light receiving area, a spatial average over the area of the light receiving surface is effected and therefore, only a small fluctuation can be detected. In the present embodiment, the field of view of the photodetector 11 is limited by means of the collimator 10 having the pin holes, so that the fluctuation can be detected with a very high sensitivity. The above equation (1) can be satisfied by providing the collimator 10 with pin holes having diameters of 0.3 mm and separated from each other by a distance of 30 cm, and with an air medium inside the collimator having a refractive index n=1.

Figure 3:
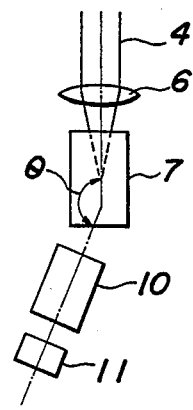
FIG. 3 is a schematic block diagram of another embodiment of apparatus for performing the method according to the invention.

In the embodiment shown in FIG. 1, the light beam 4 impinging upon the cell 7 is directed at right angles with respect to the optical axis of the collimator 10, so that the incident light flux is not directly introduced into the photodetector 11. This is called the homodyne method. According to the invention, it is also possible to use the heterodyne method in which a part of the incident light flux is made incident upon the photodetector 11. According to the invention an inclination angle $\theta$ between the incident light beam 4 and the optical axis of the collimator 10 shown in FIG. 3 may be determined at will. In the homodyne arrangement shown in FIG. 1, the output signal from the photodetector 11 is proportional to a mean square value $\overline{E_s^2}$ where $\overline{E_s}$ is the intensity of the electric field of the scattered light. In the heterodyne arrangement illustrated in FIG. 3, in which the inclination angle $\theta$ is zero, the output signal from the photodetector 11 is expressed as follows:

$$\overline{(E_e+E_s)^2} = \overline{E_e^2} + 2\overline{E_e \cdot E_s} + \overline{E_s^2}$$

wherein $\overline{E_e}$ is the intensity of the electric field of the direct incident light. $\overline{E_e}$ does not fluctuate at all or fluctuates only slowly as compared with the fluctuation of the scattered light, while the last two terms in the right-hand side of the above equation fluctuate. Since the scattered light intensity is much weaker than the incident light, $2\overline{E_e \cdot E_s} >> \overline{E_s^2}$. That is to say, even in the heterodyne method, it is possible to derive an output signal substantially proportional to the amplitude $\overline{E_s}$ of the electric field of the scattered light.

Further, it should be noted that the collimator 10 is not limited to the embodiment described above, but may be constructed in various forms as long as the field of view of the photodetector 11 can be confined to be smaller than one speckle pattern.

Now the signal processing will be explained. The output signal from the photodetector 11 is supplied to the data processing device 14 via the low pass filter 16 and is processed therein together with the output monitor signal from the photodetector 8 to derive the power spectrum density of the fluctuation in intensity of the scattered light. A power spectrum density S(f) of the stationary stochastic process x(t) may be expressed as follows.

$$S(f) = \lim_{T \to \infty} \frac{1}{2T} \left< \left| \int_{-T}^{T} x(t) e^{-2\pi i f t} dt \right|^2 \right> \quad (2)$$

On a basis of this equation (2), the Fourier transformation is performed to calculate the power spectrum density. The output signal from the photodetector 11 is amplified by the low noise amplifier 15 in such a manner that signal values can cover a wide range of A/D conversion quantum levels, and data thus quantized is processed by a microprocessor to derive the power spectrum density. From the power spectrum density, the condition of the immunological reaction is measured, as will be explained later below and is displayed numerically on the display unit 20.

Figure 4:
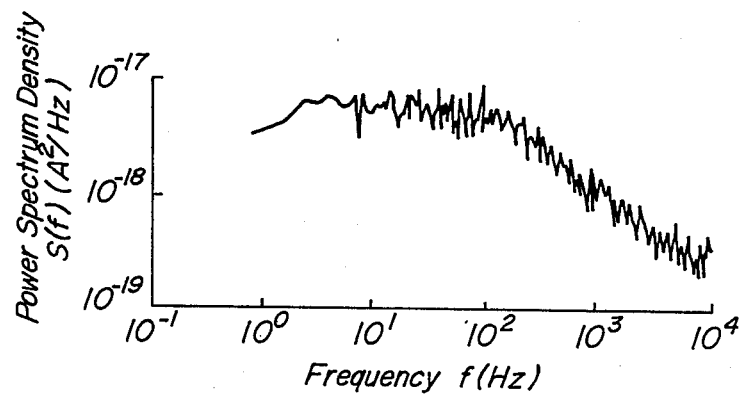
FIG. 4 is a graph showing a power spectrum density of light scattered by latex particles having an average diameter of 0.212 $\mu$m.

FIG. 4 is a graph showing the power spectrum density S(f) derived by the apparatus shown in FIG. 1, for particles 9 contained in the cell 7 which are formed by spherical latex particles having an average diameter of 0.212 μm. The latex particles are poured in the test liquid at 0.23% by weight. In a power frequency range, the power spectrum density becomes white, and in a higher frequency range, the power spectrum density becomes smaller in accordance with the increase in frequency.

Now methods of deriving the white level of the power spectrum density will be explained.

In a first method, values of the power spectrum density $S(f_0)$, $S(f_1)$, $S(f_2)$, $S(f_3)$..., $S(f_n)$... at frequencies $f_0$, $f_1$, $f_2$, $f_3$..., $f_n$,... which are spaced from each other by a given distance $\Delta$ ($\Delta = f_n - f_{n-1}$), are successively compared with each other to derive differences therebetween as follows.

$$\Delta S_0 = S(f_0) - S(f_1)$$
$$\Delta S_1 = S(f_1) - S(f_2)$$
$$\vdots$$
$$\Delta S_n = S(f_n) - S(f_{n+1})$$

When a predetermined number (several to ten) of consecutive differences have positive signs successively, i.e. a predetermined number of power spectrum density values decrease continuously, a frequency fp of the first power spectrum density value of said series of values is detected as a frequency at a flection point. Then, an average value of the power spectrum density values up to the value $S(f_p)$ is calculated by the following equation.

$$\overline{S} = \frac{\sum_{i=0}^{p} S(f_i)}{p} \quad (3)$$

The average value $\overline{S}$ thus calculated is the derived white level of the power spectrum density of the fluctuation in intensity of the light scattered by the particles.

Figure 5:
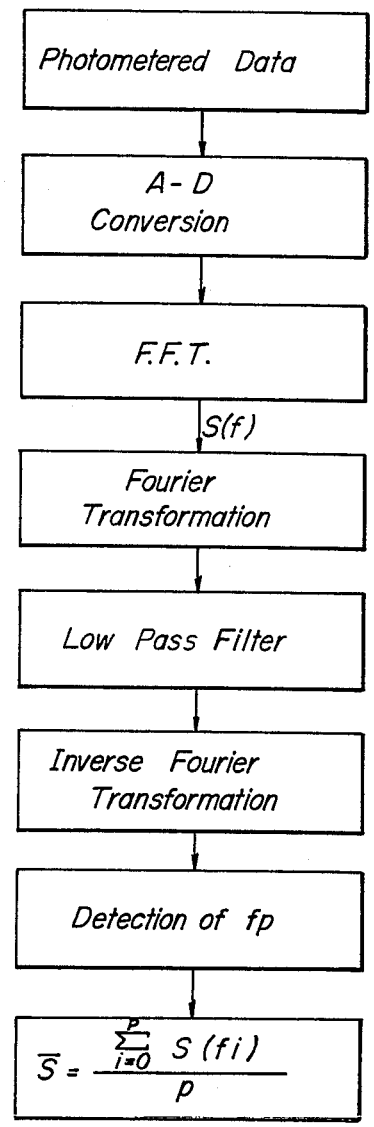
FIG. 5 is a flow chart illustrating a method for deriving a white level of the power spectrum density.

FIG. 5 is a flow chart explaining successive steps for deriving the white level in accordance with a second method. In the second method, the photoelectrically converted output signal from the photodetector 11 is processed by the amplifier 15 and the low pass filter 19 to derive an analog signal, and then the analog signal is converted by the A/D converter 17 into a digital signal. Then the digital signal is supplied to the fast Fourier transformer unit 18 to derive a power spectrum density S(f). The power spectrum density thus derived contains a number of small variations as illustrated in FIG. 6A. Then, the power spectrum density is subjected to a Fourier transformation to derive spacial frequency components as shown in FIG. 6B. Next, the spacial frequency components are passed through a digital low pass filter having a cut-off frequency $f_c$. Then the output signal from the low pass filter is subjected to an inverse Fourier transformation to derive a power spectrum density S(f) having a smooth waveform as shown in FIG. 6C. Then the smoothed power spectrum density is processed by the first method to derive the white level as the averaged power spectrum density $$\overline{S} = \frac{\sum_{i=0}^{p} S(f_i)}{p}.$$

FIGS. 7 to 9 are graphs showing the relationships between the white levels and the concentrations of there sample substances. For deriving the relationships, use was made of spherical latex particles having an average diameter of 0.212 μm and having a reagent substance coated thereon.

FIG. 7 is a graph showing the correlation obtained between the white level and the concentration of IgE. In order to derive the correlation, a plurality of standard sample liquids having known different IgE concentrations were prepared, and then reaction liquids were prepared by adding reagent liquids containing latex particles coatd with anti-IgE to the standard sample liquids. The concentration of the coated latex particles was adjusted to 0.23% by weight ($4.45 \times 10^{11}$ particles/cm$^3$) with respect to the sum of the weights of the latex particles and the liquid medium, which may be a buffer solution.

The correlation between the white level of the power spectrum density and the IgE concentration may be derived by using white level values directly obtained by the apparatus shown in FIG. 1. However, if the measuring system is not in a clean condition it might produce noise, and direct measurements cannot be carried out in a reproducible manner due to the influence of noise. Therefore, the graph illustrated in FIG. 7 was obtained by deriving a ratio of the white level after the reaction to that before the reaction. That is to say, the ordinate axis in FIG. 7 represents the white level ratio R defined as follows.

$$R = \frac{\text{white level after 15 minutes}}{\text{white level before reaction}}$$

The abscissa axis represents the IgE concentration in units of g/ml. As shown by the solid curve in FIG. 7, the white level ratio increases in accordance with the increase in the IgE concentration.

FIG. 8 is a graph showing the relationship obtained between the white level ratio and the concentration of AFP. Use was made of latex particles having anti-AFP applied thereon. The concentration of the coated latex particles was adjusted to 0.38% by weight ($7.41 \times 10^{11}$ particles/cm$^3$). The remaining conditions were entirely same as those of the experiment which produced the graph shown FIG. 7.

FIG. 9 is a graph showing the relationship obtained between the white level ratio and the CRP concentration. Use was made of latex particles coated with anti-CRP. The concentration of particles was set to 0.40% by weight ($7.65 \times 10^{11}$ particles/cm$^3$). In this case, the white level ratio R was derived by the following equation because of experimental convenience.

$$R = \frac{\text{white level after 15 minutes}}{\text{white level at start of reaction}}$$

The remaining conditions were entirely same as those of the previous experiments. From the graph shown in FIG. 9, the white level ratio R increases in accordance with the increase in the CRP concentration up to $10^{-6}$ g/ml, but after that the ratio R decreases in accordance with the increase in the CRP concentration. This is due to the fact that the reaction is suppressed by the large concentration of CRP.

As explained above, the concentration of sample substances and the white level of the power spectrum density has a given relationship, so that this relationship can be utilized as a calibration curve. Therefore when a relationship has been previously determined by using standard samples having known different concentrations of sample substances to be measured, it is possible to measure an unknown concentration of sample substances contained in a sample by measuring the white level or white level ratio of the power spectrum density of light scattered by particles contained in a test liquid in which reagent substances are added at a given constant concentration.

In the embodiments so far explained, the power spectrum density of light scattered by the agglutinated latex particles contained in the reaction liquid is measured with the aid of the apparatus shown in FIG. 1. According to the invention, it is possible to use any apparatus which can measure the power spectrum density from the intensity of light scattered by particulate substances. An example of one such apparatus is illustrated in FIG. 10.

In the embodiment of FIG. 10, elements similar to those shown in FIG. 1 are denoted by the same reference numerals used in FIG. 1, and detailed explanation thereof is omitted. In this embodiment, a polarizer 21 and an analyzer 22 are disposed on an axis of the light beam 4 before and after the cell 7, respectively. The analyzer 22 transmits only a polarized component having a polarizing direction perpendicular to the polarizing direction of the polarizer 21. Therefore, the photodetector 11 detects only a cross polarization component of the linearly polarized light impinging upon the cell 7. Light scattered at 180° (in a forward direction) by a spherical particle has polarized components which are parallel to the polarization of as the incident light, so that such scattered light is blacked by the polarizing plate 22. In contrast, since multiple-scattered light by spherical particles and scattered light of agglutinated particles having optical anisotropy have different polarized components than the incident light, such scattered light is transmitted through the analyzer 22. Therefore, the power spectrum density is derived from cross polarization of the forward scattered light, and then the concentration of sample substances is measured by the white level of the thus detected power spectrum density.

In the above embodiments, the reagent substances are bound on the surfaces of spherical latex particles, but the present invention is not limited to such embodiments. For instance, if reagent substances cause the scattering, it is not necessary to use insoluble carries such as latex particles.

As explained above, according to the invention a concentration of specific substances contained in a sample can be measured by deriving a white level or white level ratio of a power spectrum density of light scattered by complexes in a reaction liquid. Since the white level or white level ratio can be determined precisely and easily, the concentration of sample substances can be measured accurately and easily.

What is claimed is:

1. A method of measuring a concentration of substances contained in a sample on the basis of complexes which are formed by a specific reaction between the sample substances and reagent substances which are specifically reactive with said sample substances, the method comprising the steps of:
    projecting a radiation beam upon said complexes;
    detecting radiation scattered by said complexes to produce an output signal;
    processing said output signal to derive a power spectrum density of radiation scattered by said complexes;
    deriving a white level or white level ratio of the power spectrum density, said white level being a value of said power spectrum density which is substantially flat over a low frequency range, and said white level ratio being a ratio of two white levels which are measured at two different times; and
    measuring a concentration of the sample substances on the basis of the white level or white level ratio.

2. A method according to claim 1, wherein said specific reaction is a reaction between the sample substance to be measured and insoluble substances which are specifically reactive with the sample substances.

3. A method according to claim 2, wherein said insoluble substnces are formed by spherical particles on which are bound substances which are specifically reactive with said sample substances.

4. A method according to claim 3, wherein said spherical substances are formed by latex particles.

5. A method according to claim 1, wherein said step of deriving the white level or white level ratio of the power spectrum includes the steps of:
    comparing successive values $S(f_0)$, $S(f_1)$, $S(f_2)$ ... of the power spectrum density at frequencies $f_0$, $f_1$, $f_2$ ..., said frequencies being separated from each other by a constant value, to derive differences $$\Delta S_0 = S(f_0) - S(f_1), \Delta S_1 = S(f_1) - S(f_2) \ldots,$$

selecting a series of power spectrum density values which produce a predetermined number of consecutive differences having the same sign,
    selecting the first power spectrum density value $S(f_p)$ among the selected series of power spectrum density values,
    calculating an average value $\overline{S}$ of power spectrum density values up to said first power spectrum density value $S(f_p)$ in accordance with the following equation, $$\overline{S} = \frac{\sum_{i=0}^{p} S(f_i)}{p}$$

said average value $\overline{S}$ constituting the white level.

6. A method according to claim 1, wherein before deriving the white level or white level ratio, the power spectrum density is subjected to a smoothing process including the steps of:
    subjecting the power spectrum density to a Fourier transformation to derive spacial frequency components,
    filtering the spacial frequency components with a low pass filter, and
    subjecting an output signal from the low pass filter to an inverse Fourier transformation to derive a smoothed power spectrum density.

7. A method according to claim 1, wherein said radiation beam is made incident upon the reaction liquid through a polarizer, and the radiation scattered by the complexes is detected through an analyzer having a polarizing direction which is perpendicular to a polarizing direction of the polarizer.

8. A method according to claim 1, wherein said white level ratio is derived by calculating a ratio of a white level after the reaction to a white level before the reaction.

9. A method according to claim 1, wherein said white level ratio is derived by calculating a ratio of a white level after the reaction to a white level at a start of the reaction.

10. A method according to claim 1, further including, before deriving the white level or white level ratio, the step of removing a number of small variations of the power spectrum density to derive a power spectrum density having a smooth waveform.

* * * * *